United States Patent [19]
Ashida et al.

[11] Patent Number: 5,973,218
[45] Date of Patent: Oct. 26, 1999

[54] PROCESS FOR PRODUCING CYCLOOLEFIN

[75] Inventors: Keita Ashida; Mineyuki Iwasaki, both of Okayama, Japan

[73] Assignee: Asahi Kasei Kogyo Kabushiki Kaisha, Osaka, Japan

[21] Appl. No.: 09/100,949

[22] Filed: Jun. 22, 1998

[30] Foreign Application Priority Data

Jul. 8, 1997 [JP] Japan .................................. 9-182606

[51] Int. Cl.⁶ ....................................................... C07C 5/11
[52] U.S. Cl. .......................................... 585/273; 585/269
[58] Field of Search ..................... 585/273, 266, 585/269; 208/144, 145

[56] References Cited

U.S. PATENT DOCUMENTS

| | | | |
|---|---|---|---|
| 4,197,415 | 4/1980 | Hideyuki et al. | 585/23 |
| 4,734,536 | 3/1988 | Nagahara et al. | 585/269 |
| 5,157,179 | 10/1992 | Setoyama et al. | 585/266 |
| 5,569,803 | 10/1996 | Takewaki et al. | 585/269 |

FOREIGN PATENT DOCUMENTS

| | | |
|---|---|---|
| 2-16736 | 4/1990 | Japan . |
| 5-12331 | 2/1993 | Japan . |
| 8-19012 | 2/1996 | Japan . |
| 8-25919 | 3/1996 | Japan . |

OTHER PUBLICATIONS

Soede et al. "The partial hydrogenation of benzene and of toluene over ruthenium catalysts . . . ", paper presented at 3rd International Heterogenous Cata . . . Sympmosium; Studies of Science and Catalysis v78, 345–52 (Apr. 1993).

J. Struijk, et al, "Partial liquid–phase hydrogenation of benzene to cyclohexene over ruthenium catalysts in the presence of an aqueous salt solution", Applied Catalysis A:General, 89 (1992), Elsevier Science Publishers B.V., Amsterdam pp. 77–102.

*Primary Examiner*—Bekir L. Yildirim
*Attorney, Agent, or Firm*—Birch, Stewart, Kolasch & Birch, LLP

[57] ABSTRACT

A process for producing a cycloolefin by partial hydrogenation of a monocyclic aromatic hydrocarbon with hydrogen in the presence of a ruthenium catalyst, water and a metal sulfate, wherein the hydrogenation is conducted while changing the concentration of the metal sulfate dissolved in an aqueous phase in which the catalyst is present.

12 Claims, 5 Drawing Sheets

FIG. 6

PROCESS FOR PRODUCING CYCLOOLEFIN

FIELD OF THE INVENTION

The present invention relates to a process for producing a cycloolefin by partial hydrogenation of monocyclic aromatic hydrocarbons in the presence of a ruthenium catalyst.

BACKGROUND OF THE INVENTION

Cycloolefins, in particular, cyclohexene compounds are valuable as intermediates of organic chemical industrial products, and are particularly useful as starting materials for polyamides and lysine.

A variety of processes for producing cycloolefins are known and, of these processes, partial hydrogenation of monocyclic aromatic hydrocarbons in the presence of a ruthenium catalyst is most commonly employed. For improving selectivity and yield, the kinds of catalyst components and of carriers, metallic salts to be employed as additives to reaction systems and the like have been studied, and a number of results have been reported.

For example, the following suggestions have been made for the reaction systems in which water and zinc coexist and by which cycloolefins can be produced at relatively high yields.

(1) A process for partially reducing a monocyclic aromatic hydrocarbon with hydrogen in the presence of water and at least one kind of zinc compound under a neutral or acidic condition, using a particulate catalyst which mainly comprises metallic ruthenium having an average crystallite size of from 30 to 200 Å and which is supported on a carrier (JP-B-8-25919; The term "JP-B" as used herein means an "examined Japanese patent publication").

(2) A process for producing a cycloolefin by partially hydrogenating a monocyclic aromatic hydrocarbon in the presence of a ruthenium catalyst, in which at least one of a zinc oxide and a zinc hydroxide at an amount of not more than saturation solubility is present in the reaction system in a completely dissolved state (JP-B-5-12331).

(3) A process for partially reducing a monocyclic aromatic hydrocarbon with hydrogen in the presence of water, in which a reaction is conducted using hydrogenated catalyst particles mainly comprising metallic ruthenium having an average crystallite size of 200 Å or less in the presence of at least one kind of a solid basic zinc under a neutral or acidic condition (JP-B-8-19012).

(4) A process for partially reducing a monocyclic aromatic hydrocarbon with hydrogen using a ruthenium catalyst, which is prepared by reducing a ruthenium compound containing zinc beforehand, in the presence of water and a water-soluble zinc compound under an acidic condition (JP-B-2-16736).

In the process of producing a cycloolefin by partially reducing a monocyclic aromatic hydrocarbon with hydrogen using a ruthenium catalyst in the presence of water and zinc sulfate, the effect of concentration of zinc sulfate in the aqueous phase on the results of the reaction has been already examined, and it is known that there exists the most suitable zinc sulfate concentration which gives the highest selectivity of cycloolefin (Applied Catalysis A: General, 89 (1992) 77–102).

When the process of producing a cycloolefin by partially hydrogenating a monocyclic aromatic hydrocarbon with hydrogen using a ruthenium catalyst is applied to industrial practice, the catalyst is preferably used for a long time period because the frequency of catalyst replacement that may obstruct efficient production is desired to be made as less as possible. In this case, however, it was found that the selectivity of cycloolefin varies with time. After commencing the reaction using a catalyst, the selectivity of cycloolefin is generally improved at the very initial stage of the reaction, but after which the selectivity gradually decreases. The decrease in selectivity of cycloolefin, i.e., the objective product, should be avoided as much as possible for the efficient production.

However, the literature given above fails to mention any means of solving the problem regarding the decrease in the selectivity of cycloolefin caused by the long-term use of the catalyst. Even a description about the change, particularly the decrease, in selectivity of cycloolefin which is caused by the long-term use of the catalyst cannot found therein.

SUMMARY OF THE INVENTION

It is therefore an object of the present invention to provide a process for efficiently producing a cycloolefin by hydrogenation of a monocyclic aromatic hydrocarbon.

Other objects and effects of the present invention will become apparent from the following description.

As a result of extensive studies, the present inventors have found a surprising fact that, in the production of a cycloolefin by the partial hydrogenation of a monocyclic aromatic hydrocarbon with hydrogen in the presence of a ruthenium catalyst, water, and a metal sulfate, the optimum concentration of the metal sulfate dissolved in the aqueous phase which contains the catalyst varies with the long-term use of the catalyst. In view of this fact, the present inventor have succeeded to solve the problem of the decrease in cycloolefin selectivity caused by the long-term use of a ruthenium catalyst, by constantly adjusting the metal sulfate concentration in the aqueous phase of the reaction system to or closely to the optimum concentration thereof, thus accomplishing the present invention.

That is, the above described objectives of the present invention have been achieved by providing the following constitutions:

(1) A process for producing a cycloolefin by partial hydrogenation of a monocyclic aromatic hydrocarbon with hydrogen in the presence of a ruthenium catalyst, water and a metal sulfate,
wherein the hydrogenation is conducted while changing the concentration of the metal sulfate dissolved in an aqueous phase in which the catalyst is present;

(2) The process according to the above (1), wherein the hydrogenation is conducted while increasing the metal sulfate concentration;

(3) The process according to the above (1) or (2), wherein the metal sulfate comprises at least zinc sulfate;

(4) The process according to any one of the above (1) to (3), wherein the metal sulfate concentration in the aqueous phase is changed within the range of from $1\times10^{-6}$ to 5.0 mol/liter;

(5) The process according to any one of the above (1) to (4), wherein the water is present in an amount of from 0.5 to 20 times by weight that of the monocyclic aromatic hydrocarbon;

(6) The process according to any one of the above (1) to (5), wherein the ruthenium catalyst comprises metallic ruthenium prepared by reducing a ruthenium compound beforehand;

(7) The process according to the above (6), wherein the ruthenium catalyst is a non-supported catalyst and the metallic ruthenium has an average crystallite size of 200 Å or less; and (8) The process according to the above (7), wherein the ruthenium compound comprises a zinc compound, and the content of zinc is from 0.1 to 50% by weight based on the weight of ruthenium.

DETAILED DESCRIPTION OF THE INVENTION

The present invention is described in detail below.

Examples of the monocyclic aromatic hydrocarbon for use in the present invention as a starting material include benzene, toluene, xylenes, and benzenes substituted by an alkyl group having generally from 1 to 4 carbon atoms.

In the present invention, the reaction pressure is generally from 10 to 200 atm and preferably from 20 to 70 atm. Too low reaction pressure results in lowering the cycloolefin selectivity, while too high pressure necessitates that hydrogen and a monocyclic aromatic hydrocarbon to be fed into a reactor are of high pressure, either of which are inefficient.

In the present invention, the reaction temperature is generally from 50 to 250° C. and preferably from 100 to 200° C. Too low temperature causes the reaction rate to decrease, whereas too high temperature results in promoting growth of the average crystallite size of ruthenium acting as catalyst.

The ruthenium catalyst for use in the present invention are generally those comprising metallic ruthenium prepared by reducing various ruthenium compounds beforehand. Examples of such ruthenium compounds include its halides such as chloride, bromide and iodide; nitrate; sulfate; hydroxide; and various complexes including ruthenium such as ruthenium carbonyl complex, ruthenium acetylacetonato complex, ruthenocene, ruthenium ammine complex and compounds derived from such complexes. These ruthenium compounds may be used as a mixture of two or more thereof.

The method of reducing the ruthenium compound includes contact reduction with hydrogen, carbon monoxide, etc. and chemical reduction with formalin, sodium boron hydride, hydrazine, etc. Of these, the catalytic reduction with hydrogen is preferred, and the reduction is usually performed at a temperature of from 50 to 450° C., and preferably of from 100 to 400° C. Reduction temperature not higher than 50° C. requires too much time for the reduction whereas exceeding 450° C. may result in promoting the aggregation of ruthenium particles to have an adverse effect on the activity or selectivity. The reduction can be performed both in a gas phase and in a liquid phase, but preferably performed in the liquid phase, because the reduction in the liquid phase makes it possible to remove impurities which exert an adverse influence on the reaction at the same time.

Catalysts mainly comprising ruthenium prepared by adding another metal or metallic compound to a ruthenium compound either before or after the reduction thereof may also be employed in the present invention. Examples of the metal and metallic compound include zinc, chromium, molybdenum, tungsten, manganese, cobalt, nickel, iron, copper, gold, palladium, and compounds of these metals. When these metals or metallic compounds are employed, the atomic ratio thereof to ruthenium atom usually falls in the range of from 0.001 to 20. Of the above-enumerated metal and metal compounds, zinc or zinc compounds are preferred, and they are preferably added to a ruthenium compound before the reduction thereof. The content of zinc particularly preferably is from 0.1 to 50% by weight based on the weight of ruthenium.

The ruthenium catalyst for use in the present invention may be supported on a carrier. The carrier is not particularly limited, and examples thereof include metals such as magnesium, aluminum, silicon, calcium, titanium, vanadium, chromium, manganese, cobalt, iron, nickel, copper, zinc, zirconium, hafnium, and tungsten; the oxides, composite oxides, hydroxides, sulfates, water-insoluble metallic salts of these metals; and compounds and mixtures formed by chemical or physical combination of two or more kinds of these carriers. Techniques for supporting ruthenium on these carriers are not particularly limited, and techniques such as adsorption, ion exchange, immersion, coprecipitation, dryness, and the like can be exemplified. Although it is also not particularly limited, the supported amount of ruthenium is generally from 0.001 to 20% by weight based on the weight of the carrier. It is preferred, however, to employ ruthenium as it is without supporting on a carrier.

Furthermore, in the case where a non-supported ruthenium catalyst which comprises metallic ruthenium prepared by reducing a ruthenium compound beforehand is used as the ruthenium catalyst, the metallic ruthenium preferably has an average crystallite size of 200 Å or less. An average crystallite size exceeding 200 Å causes reduction in the ruthenium catalyst surface area, on which the active point of the reaction is present, to thereby decrease the catalytic activity, thus making the reaction inefficient. The average crystallite size of the ruthenium catalyst is calculated with Scherrer's formula from the expansion of the diffraction line width obtained by X-ray diffraction. Specifically, the value is calculated from the expansion of the diffraction angle ($2\theta$) that has a maximum in the vicinity of 44° when a CuK$\alpha$ line is used as the X-ray source. The lower limit of the average crystallite size is theoretically larger than the crystalline unit and is practically 10 Å or larger.

The amount of the ruthenium catalyst to be used in the present invention depends on the amount of the water that is present in the reaction system, and is expressed as the weight of the ruthenium catalyst per unit volume of the water phase formed by the water. Specifically, from 0.01 to 100 g of the ruthenium catalyst can be preferably used per 1000 ml of the water phase.

Water must be present in the reaction system of the present invention. Although it varies depending on the types of the reaction, the amount of the water to be used is generally from 0.001 to 100 times by weight the weight of the monocyclic aromatic hydrocarbon employed as a starting material. Too little water causes the cycloolefin selectivity to lower whereas too much water causes disadvantages such as necessitating a larger reactor. Therefore, it is preferred that water is present in a reactor in an amount of 0.5 to 20 times by weight the weight of the monocyclic aromatic hydrocarbon employed as a starting material. In either case, it is necessary, however, that water is present in an amount enough to prevent a liquid phase comprising water and an organic liquid phase comprising the starting material and products as major components from mingling with each other into one phase under reaction conditions. In other words, water must be present in an amount enough to maintain a state where the organic liquid phase mainly comprising the starting material and products, i.e., the oil phase, is separated from the aqueous phase comprising water as a major component, that is, two phases of the oil phase and the aqueous phase are simultaneously present. The major components as used herein mean components having the maximum molar ratio of components composing the respective liquid phases.

The hydrogen ion concentration, i.e., pH, of the aqueous phase formed by water that coexists in the reaction system is preferably 7.0 or less, that is, acidic or neutral.

Furthermore, in the present invention, the presence of a metal sulfate is required. In the reaction system, it is not particularly required that the entire amount of the metal sulfate be present as solid, but at least part or the entire amount thereof may be present in a dissolved condition. Examples of metal that is used as a metal sulfate in the reaction system include zinc, iron, nickel, cadmium, gallium, indium, magnesium, aluminum, chromium, manganese, cobalt and copper. Two or more kinds of these metal sulfates can be employed in combination. Further, double salts containing such metal sulfates can also be used. Zinc sulfate is particularly preferably used as the metal sulfate. The amount of the metal sulfate employed is preferably such that gives the metal sulfate concentration of from $1 \times 10^{-5}$ to 5.0 mol/liter in the aqueous phase that is present in the reaction system. When at least zinc sulfate is employed as the metal sulfate, the concentration is more preferably from $1 \times 10^{-3}$ to 2.0 mol/liter.

Similar to known processes, the following metallic salts can be present in the reaction system of the present invention. Examples thereof include metallic nitrates, chlorides, oxides, hydroxides, acetates and phosphates of metals selected from: metals of group 1 in the periodic table such as lithium, sodium and potassium; metals of group 2 such as magnesium and calcium (Numbering of the groups is according to IUPAC Nomenclature of Inorganic Chemistry, Revised Edition (1989)); and zinc, manganese, cobalt, copper, cadmium, lead, arsenic, iron, gallium, germanium, vanadium, chromium, silver, gold, platinum, nickel, palladium, barium, aluminum, etc. Two or more kinds of these metallic salts can also be chemically and/or physically mixed and employed. Of these metallic salts, zinc salts such as zinc hydroxide and zinc oxide are preferably added to the reaction system and, particularly, the presence of double salts containing zinc hydroxide, for example, those represented by the general formula $(ZnSO_4)_m \cdot (Zn(OH)_2)_n$ (where m : n=1:0.01 to 1:100) in the reaction system are preferred.

The amount of these metallic salts employed is not particularly limited as long as the aqueous phase is kept acidic or neutral. However, it is usually from $1 \times 10^{-5}$ to $1 \times 10^5$ times by weight the weight of ruthenium employed. These salts can be present in any place within the reaction system, and it is not required that the entire amount thereof is dissolved in the aqueous phase.

Besides water, one or more kinds of organic substances having one or more hydroxyl groups can be present in the reaction system. The amount of the organic substance is not particularly limited. However, when the organic substance can dissolve therein under the reaction conditions both water and organic matters including a monocyclic aromatic hydrocarbon starting material and a cycloolefin and a cycloalkane derived therefrom, it is preferred to adjust the amount of the hydroxyl group-containing organic substances so that the aqueous phase and oil phase in the reaction system do not mingle with each other to form into one phase. That is, the addition amount of said organic substances is preferably in the range that permit the reaction liquid to constitute two different phases, i.e., the aqueous phase and the oil phase.

In the process for producing a cycloolefin by the partial hydrogenation of a monocyclic aromatic hydrocarbon with hydrogen in the presence of a ruthenium catalyst, water, and a metal sulfate, the important characteristic of the present invention resides in that the reaction is conducted while changing the metal sulfate concentration in the aqueous phase in which the catalyst is present. Preferably, the reaction is conducted while increasing the metal sulfate concentration.

When the process for producing a cycloolefin by the partial hydrogenation of a monocyclic aromatic hydrocarbon with hydrogen by the use of the ruthenium catalyst is industrially practiced, it is desirable that the reaction is carried out under conditions where formation of by-produced cycloparaffin is suppressed and the selectivity of desired cycloolefin is kept as high as possible. Therefore, the reaction should be usually carried out under conditions where the concentration of the metal sulfate in the aqueous phase that is present in the reaction system provides the highest or nearly highest selectivity of cycloolefin. However, there has hitherto been no knowledge that the optimum concentration of the metal sulfate varies during the long-term use of the catalyst. Moreover, the fact that the optimum concentration changes itself has been beyond expectation in general.

The experiments made by the present inventors confirmed for the first time that the optimum concentration of the metal sulfate varies during the long-term use of the catalyst, i.e., that the long-term use of the catalyst changes the metal sulfate concentration in the aqueous phase which gives the maximum cycloolefin selectivity. Thus, the present inventors has identified one of causes of the reduction in cycloolefin selectivity observed during the long-term use of the catalyst, at the same time, succeeded in greatly suppressing the decrease in the selectivity.

That is, a cycloolefin can be produced at the highest or nearly highest selectivity by adjusting the concentration of the metal sulfate in the aqueous phase to the optimum metal sulfate concentration which varies during the long-term use of the catalyst. The effect of improving the cycloolefin selectivity is considered to be very important, because it gives an improvement in annual cycloolefin production as estimated at a scale of several thousands tons in view of the standard-scale facilities for industrial cycloolefin production of about a hundred thousand tons per year.

The metal sulfate concentration which gives the maximum cycloolefin selectivity can be confirmed by drawing out part of a catalyst slurry containing a ruthenium catalyst from the reaction system at suitable intervals, adding water or the metal sulfate of the same kind as employed in the reaction to the drawn catalyst slurry to prepare a catalyst slurry having a different metal sulfate concentration, and evaluating reactions using such a catalyst slurry by means of a batch experiment.

Since the concentration which gives the maximum cycloolefin selectivity can be found as a result of the above experiment, the adjustment of the metal sulfate concentration in the reaction system may be carried out so that the concentration is brought close to the concentration which gives the maximum cycloolefin selectivity. Examples of a specific means for adjusting the metal sulfate concentration is described below. In the case where the metal sulfate concentration is to be increased, the increase is readily attained by the addition of the metal sulfate to the reaction system. Then, the addition of the metal sulfate may be carried out by adding a metal sulfate dissolved in or mixed with water to the reaction system. In the case where the metal sulfate concentration is to be decreased, the procedure which may be used comprises drawing part of the catalyst slurry out of the reaction system, allowing the drawn catalyst slurry to stand to cause sedimentation, replacing the resulting supernatant containing the metal sulfate dissolved therein with water, and returning the resulting catalyst slurry to the reaction system. For the adjusting procedure, simple and easily means can be appropriately selected in accordance with a reaction type employed.

The reason why the phenomenon pointed out by the present invention (i.e., the phenomenon that the metal sulfate concentration which gives the maximum cycloolefin selectivity varies) occurs, has not sufficiently been clarified yet. However, this can be considered as attributed to some changes in the active point of the ruthenium catalyst which may suffer by the exposure to reaction conditions over a long period of time.

In general, the catalytic activity is also improved according to the present invention. Thus, the process of the present invention is considered to be very efficient. As indicated also in Reference Examples, when the concentration of a metal sulfate is changed so as to improve more the selectivity of cycloolefin according to the process of the present invention, the catalytic activity is also improved at the same time. Consequently, more prolonged use of the catalyst also becomes possible.

The process of the present invention can be applied to both of a batch reaction system and a continuous reaction system. The process is particularly useful for the continuous reaction system in which there is few chances to exchange the catalyst.

When the process of the present invention is applied to a continuous reaction system, the conversion rate of the starting material is generally appropriately selected from 10 to 90 mol %, preferably from 30 to 70 mol % in view of the economical standpoint.

According to the process of the present invention, the production of a cycloolefin can be efficiently carried out over a long period of time up to 100 hours. However, it is not necessary that the reaction be continuous all over the reaction time. In short, the issue is how long the catalyst employed is exposed to reaction conditions.

The present invention will be described in detail with reference to the following Examples, but should not be construed as being limited thereto.

The conversion rates of benzene and the selectivities of cyclohexene shown in the following Examples are calculated from the following formula based on the analytical data of the concentration experiments:

Selectivity of Cyclohexene (%)

=(Mol number of cyclohexene formed by the reaction/ P)×100

P (mol number)

=(Mol number of cyclohexene formed by the reaction)

+(Mol number of cyclohexane formed by the reaction)

Conversion Rate of Benzene (%)

={(Mol number of benzene consumed in the reaction)/ (Mol number of benzene supplied to the reactor)}×100

Figure 3:
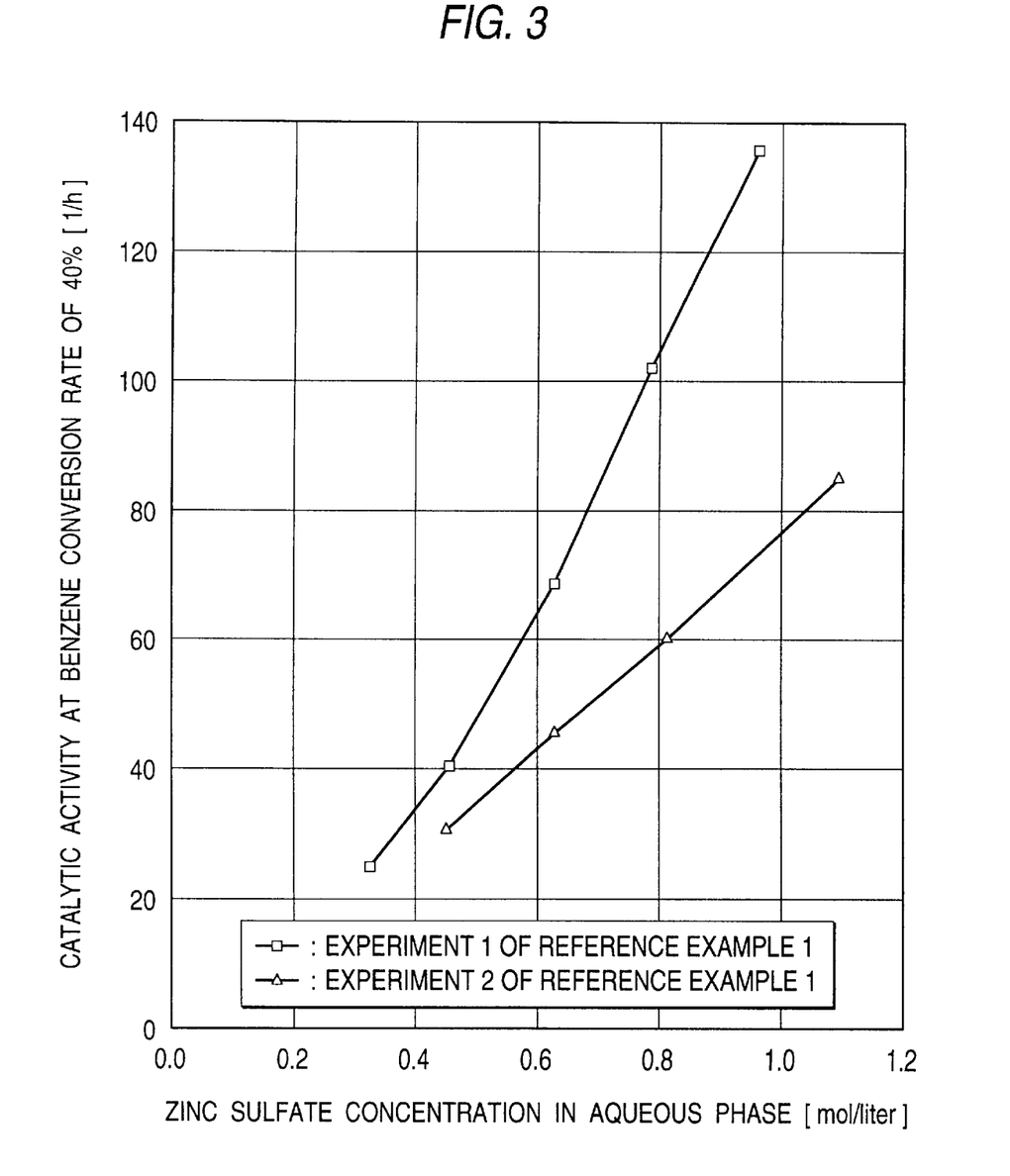
FIG. 3 is a graph showing the relations between the concentration of zinc sulfate in the aqueous phase and the consuming rate by weight of benzene per unit weight of the catalyst (i.e., the catalytic activity) at a benzene conversion rate of 40 mol % according to Experiments 1 and 2 performed in Reference Example 1.
Figure 4:
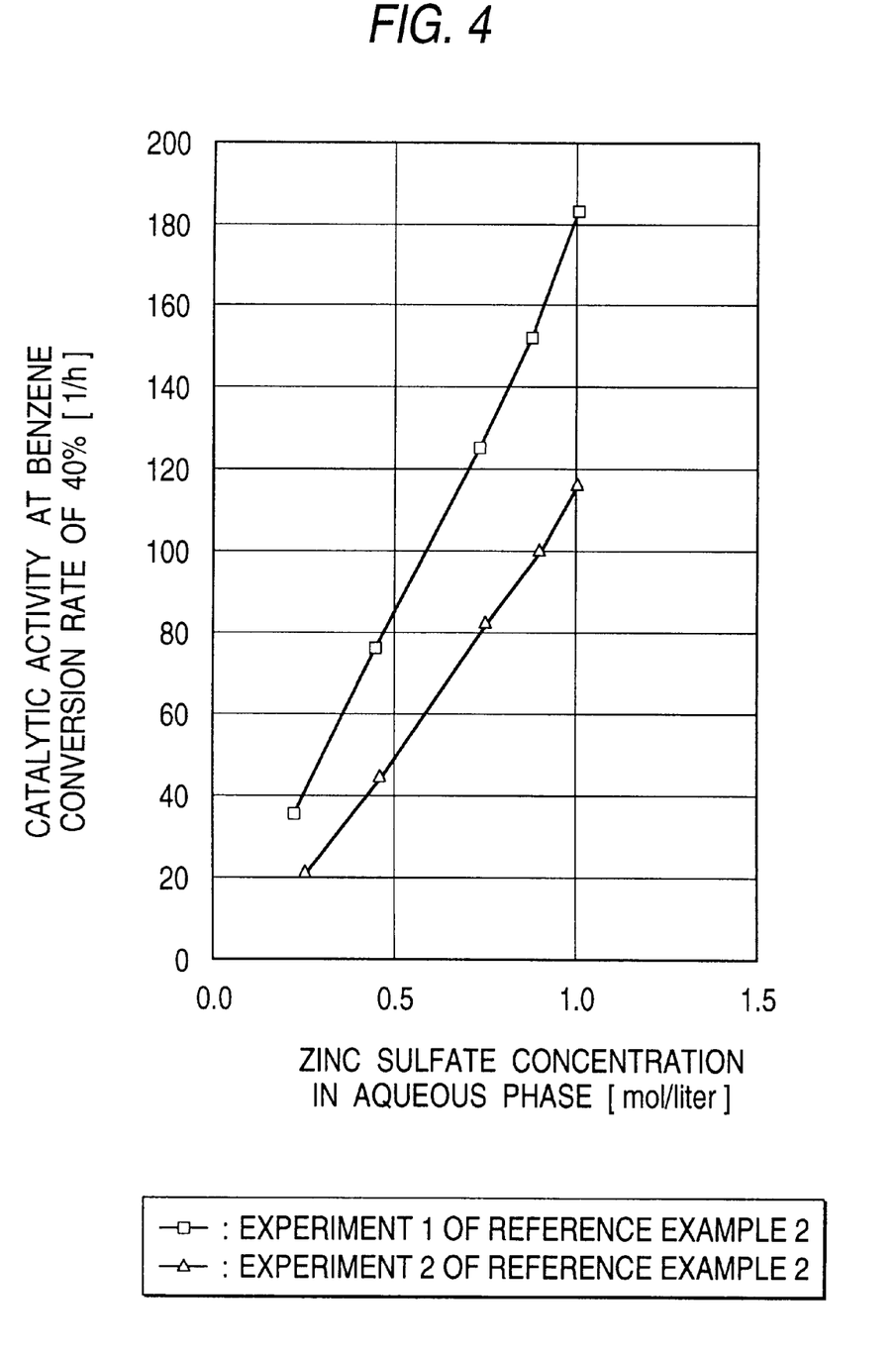
FIG. 4 is a graph showing the relations between the concentration of zinc sulfate in the aqueous phase and the consuming rate by weight of benzene per unit weight of the catalyst (i.e., the catalytic activity) at a benzene conversion of rate 40 mol % according to Experiments 1 and 2 performed in Reference Example 2.

The catalytic activities measured at a benzene conversion rate of 40% are shown in FIGS. 3 and 4. The formula used for the calculation of the catalytic activity is as follows.

Catalytic Activity at Benzene Conversion Rate of 40% (1/h)

=(Weight (g) of benzene reacted per 1 hour at benzene conversion rate of 40%)/(Weight (g) of ruthenium catalyst used in the reaction)

REFERENCE EXAMPLE 1

(Experiment 1):

Using a continuous type reactor equipped with an electromagnetic induction stirrer, with which continuous feeding of benzene and hydrogen, continuous drawing of a catalyst slurry and oil containing unreacted benzene to separate from each other, and continuous returning the separated catalyst slurry thereinto can be conducted, a continuous reaction was carried out with high-speed stirring over a period of 100 hr. After the 100 hr continuous reaction, the catalyst slurry was recovered and five 280 ml portions were separated therefrom.

Next, different amounts of zinc sulfate or different amounts of water were added to these five catalyst slurries to prepare catalyst slurries different in concentrations of zinc sulfate, respectively. For unifying their volumes, the catalyst slurries were subsequently allowed to stand to cause sedimentation, and the supernatants were appropriately removed to adjust all their volumes to 280 ml at normal a temperature and at a normal pressure. These resulting catalyst slurries were, in turn, subjected to a batch reaction according to the following procedure to examine the relations between the zinc sulfate concentration in the aqueous phase in the slurries and the cyclohexene selectivity.

The batch reaction was carried out as follows: 280 ml portion of the catalyst slurry was placed in an autoclave with 1-liter capacity which inside surface is coated with Teflon, the inner gas was adequately replaced by hydrogen, and then the reaction vessel was sealed, and heated up to 130° C. with high-speed stirring by an inductive method. High-pressure hydrogen was then introduced into the vessel up to 50 atm and, immediately after this high pressure is attained, 140 ml of liquid benzene at 130° C. was fed by pressure into the autoclave at a time. The reaction was carried out with high-speed stirring at a reaction pressure of 50 atm and at 130° C., while feeding hydrogen by pressure into the autoclave.

Figure 1:
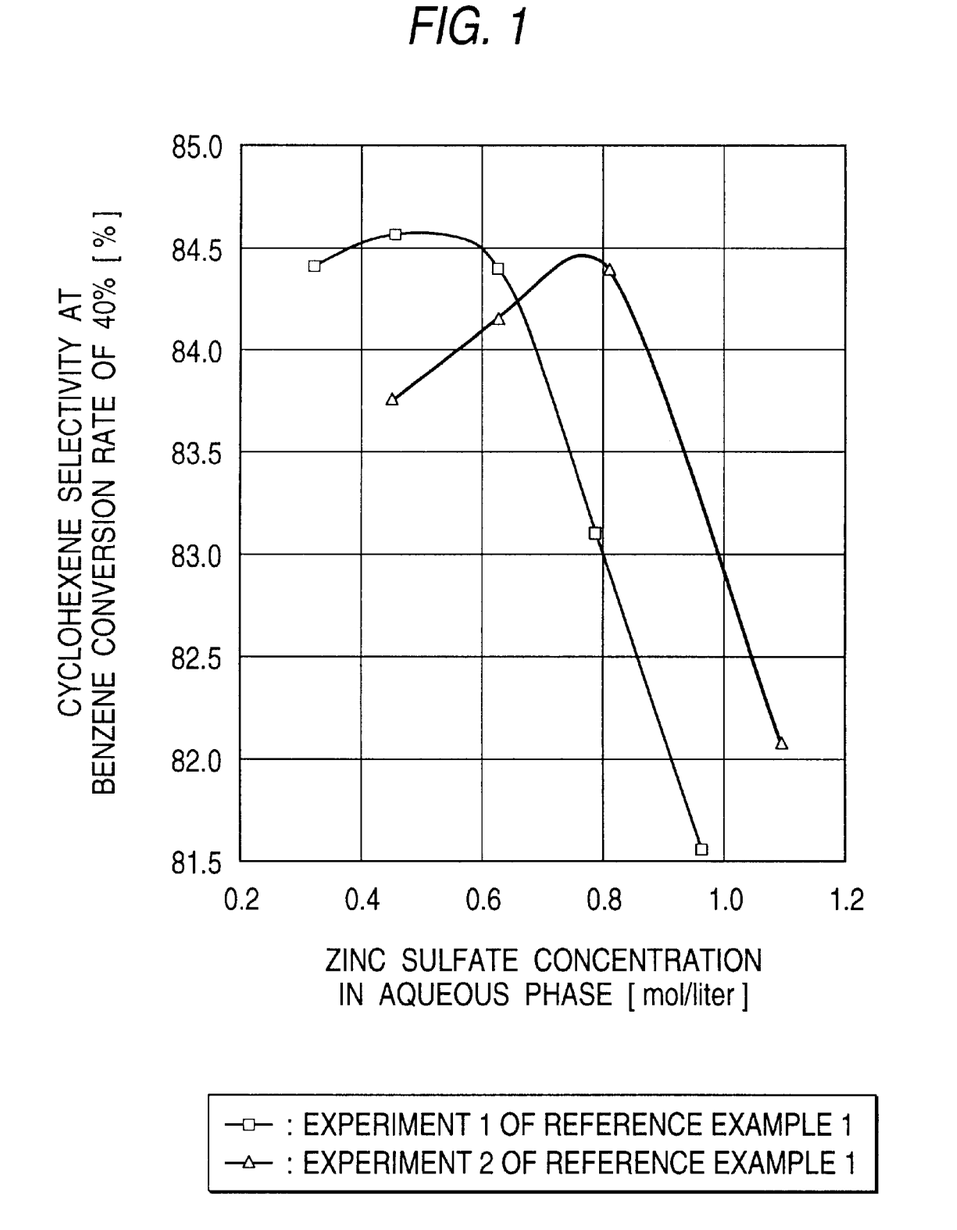
FIG. 1 is a graph showing the relations between the concentration of zinc sulfate in the aqueous phase and the selectivity of cyclohexene at a benzene conversion rate of 40 mol % according to Experiments 1 and 2 performed in Reference Example 1.

During the batch reaction, part of the reaction liquid was drawn from the autoclave at suitable intervals to check the oil composition by gas chromatography. The selectivity of cyclohexene at a benzene conversion rate of 40 mol % was found by interpolating the analytical values obtained by the gas chromatography. Furthermore, after the batch reaction, the catalyst slurry was recovered, and zinc sulfate which was dissolved in the aqueous phase in the slurry at a normal temperature and at a normal pressure was analyzed by atomic absorption spectrometry. The results obtained are shown in FIG. 1.

(Experiment 2):

The reaction was carried out in a manner similar to that of Experiment 1, except that the reaction time in the continuous type reactor was changed to 1500 hr. The results are shown in FIG. 1.

In Experiments 1 and 2 of Reference Example 1, the catalyst slurry employed in the continuous type reactor composed of 15 g of a ruthenium catalyst (average crystallite size: about 58 Å) containing 6% by weight of zinc which was prepared by reducing ruthenium hydroxide containing zinc hydroxide beforehand, 70 g of zirconia (average crystallite size: about 200 Å) as a dispersant, 1500 ml of water, and 265 g of $ZnSO_4.7H_2O$ (extra fine grade, manufactured by Wako Pure Chemical Industries Ltd.). Water contained in the formed oil which was drawn during the continuous reaction was separated by cooling and returned to the reactor to prevent water in the catalyst slurry and zinc sulfate dissolved therein from decreasing.

Furthermore, the continuous type reactor was an autoclave with 3-liter capacity which inside surface was coated with Teflon, the feed rate of benzene was 250 ml/hr during the continuous reaction, and the rate of drawing the catalyst slurry and the formed oil containing unreacted benzene from the reactor was at a rate of 1000 ml/hr.

In these experiments, the whole reaction was carried out under conditions where two different liquid phases of an oil phase and an aqueous phase are present, and the pH of the aqueous phase was acidic or neutral throughout the reaction.

The results of Reference Example 1 as shown in FIG. 1 reveals that the zinc sulfate concentration in the aqueous phase which gives highest cyclohexene selectivity at a benzene conversion rate of 40 mol % is in the range of from 0.4 to 0.6 mol/liter in the case of the catalyst slurry after subjected to 100-hr continuous reaction, whereas it shifts to the range of from 0.7 to 0.9 mol/liter in the case of the catalyst slurry after subjected to 1500-hr continuous reaction. From these facts, it is apparent that the concentration of zinc sulfate in the aqueous phase which gives the highest cyclohexene selectivity varies. That is, it can be understood therefrom that it is important to change the concentration of zinc sulfate in the aqueous phase in order to keep the selectivity high.

REFERENCE EXAMPLE 2

Experiments were carried out in a manner similar to those of Reference Example 1, except that a ruthenium catalyst (average crystallite size: about 59 Å) prepared by reducing ruthenium hydroxide containing no zinc was employed. The results obtained are shown in FIG. 2.

In these experiments, the whole reaction was carried out under conditions where two different liquid phases of an oil phase and an aqueous phase are present, and the aqueous phase was acidic or neutral throughout the reaction.

Figure 2:
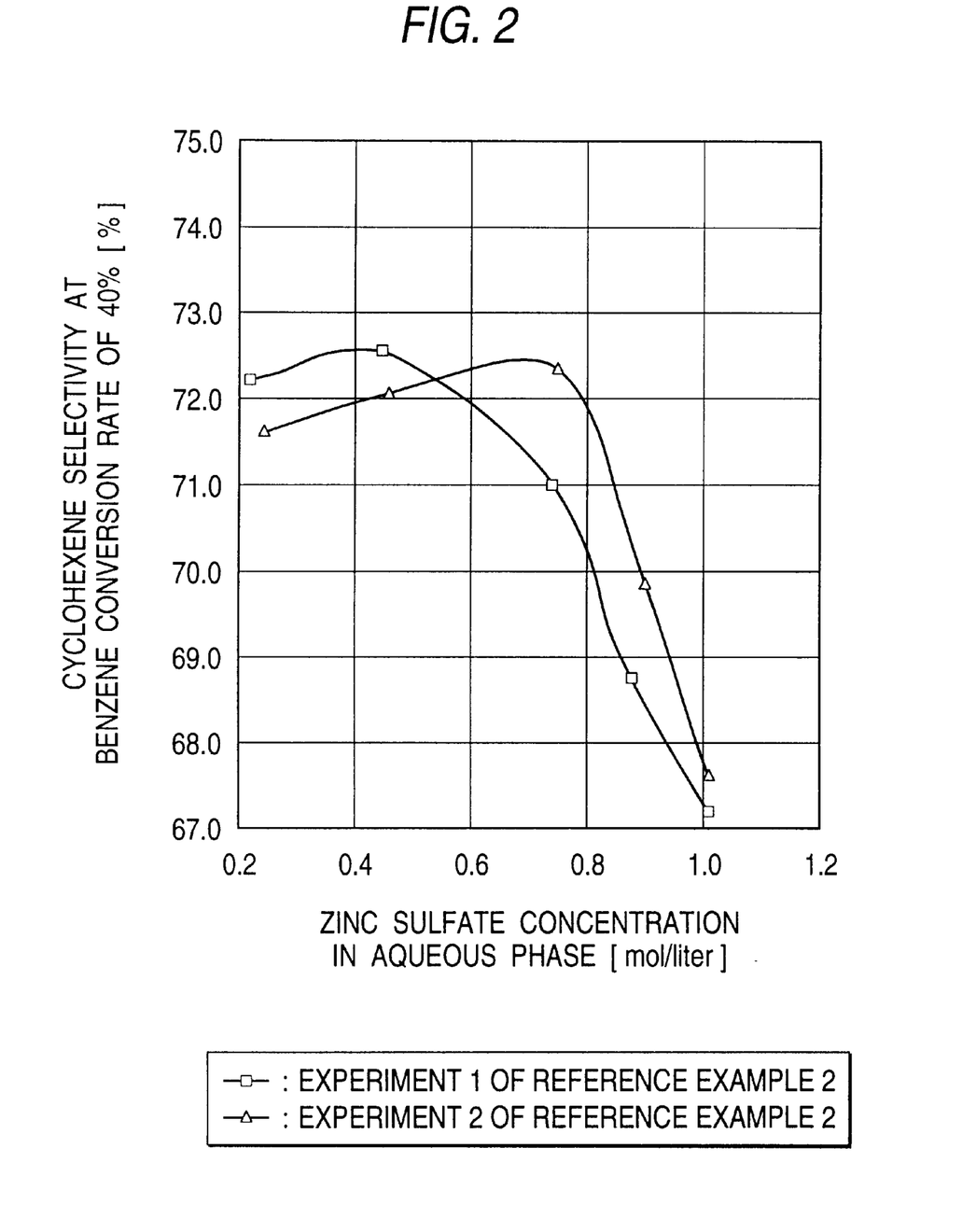
FIG. 2 is a graph showing the relations between the concentration of zinc sulfate in the aqueous phase and the selectivity of cyclohexene at a benzene conversion rate of 40 mol % according to Experiments 1 and 2 performed in Reference Example 2.

The result of Reference Example 2 as shown in FIG. 2 reveals that the zinc sulfate concentration in the aqueous phase which gives highest cyclohexene selectivity at a benzene conversion rate of 40 mol % is in the range of from 0.3 to 0.5 mol/liter in the case of the catalyst slurry after subjected to 100-hr continuous reaction, whereas it shifts to the range of from 0.6 to 0.9 mol/liter in the case of the catalyst slurry after subjected to 1500-hr continuous reaction. From these facts, it is apparent that the concentration of zinc sulfate in the aqueous phase which gives the highest cyclohexene selectivity varies.

Similar tendency as shown in FIGS. 1 and 2 can also be found at benzene conversion rates other than 40 mol %.

From the above described results, it can be understood that it is very useful to appropriately change with time the concentration of zinc sulfate, i.e., the concentration of a metal sulfate, in the aqueous phase in order to keep the cyclohexene selectivity high in the long-term use of the ruthenium catalyst. In addition, as shown in FIG. 3 and FIG. 4, in the vicinity of the metal sulfate concentration which gives the highest cycloolefin selectivity, higher concentration of a metal sulfate provides higher catalytic activity. Consequently, when the concentration of the metal sulfate is increased for keeping the cycloolefin selectivity high, this improves not only the cycloolefin selectivity but also the catalytic activity, thus making it possible to produce a cycloolefin more efficiently.

EXAMPLE 1

An experiment was conducted to attempt to suppress the cycloolefin selectivity from decreasing with time by changing the zinc sulfate concentration in the aqueous phase during the continuous reaction. After a catalyst slurry composed of 5.0 g of the ruthenium catalyst as used in Reference Example 1, 25 g of zirconia, 1500 ml of water and $ZnSO_4.7H_2O$ (extra fine grade, manufactured by Wako Pure Chemical Industries Ltd.) was placed and sealed in a reactor, the air of the gas phase in the reactor was sufficiently displaced by hydrogen. The slurry in the reactor was then heated to 130° C. and the pressure was adjusted to 50 atm by feeding hydrogen into the reactor by pressure. Benzene was continuously fed into the reactor under these conditions to initiate the reaction with high-speed stirring. Hydrogen was continuously supplemented in an amount consumed by the reaction and the formed oil containing unreacted benzene was continuously drawn from the reactor. The water and a trace amount of the metal salt contained in this oil were all recovered and appropriately returned to the reactor. Further, the compositions of the drawn oils were appropriately examined by gas chromatography and the amount of benzene continuously fed into the reactor was adjusted so that the concentration of benzene contained in the oil was kept 40 mol %.

Figure 5:
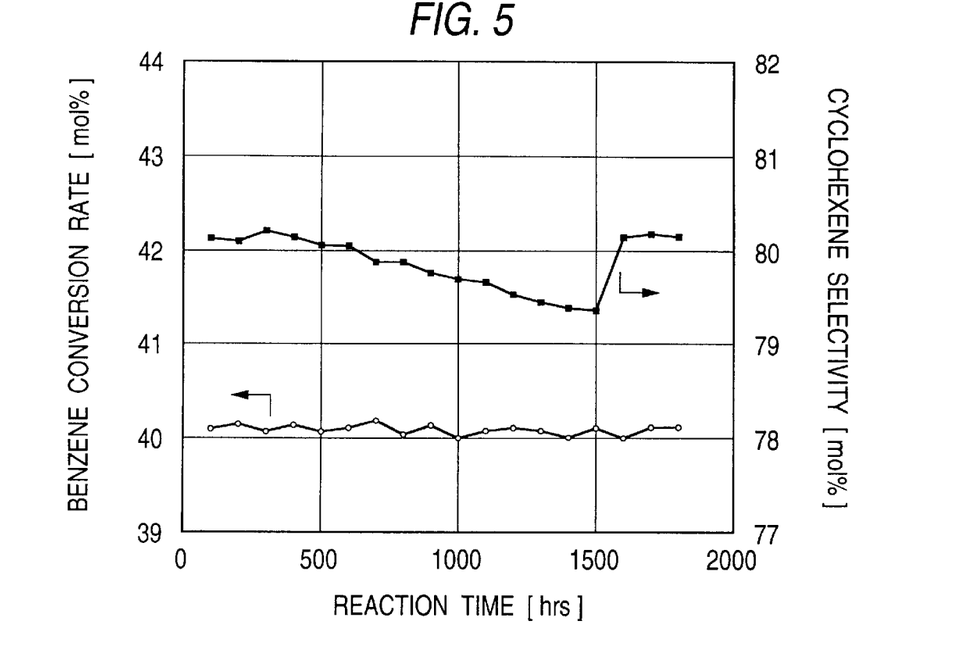
FIG. 5 is a graph showing the changes with time in the benzene conversion rate and in the cycloolefin selectivity which are calculated from the composition analyses of the oil drawn from the reactor in Example 1.

After the elapse of 1500 hr since the reaction starts, zinc sulfate was supplied to the reactor so as to give a zinc sulfate concentration in the aqueous phase of 0.8 mol/liter. The results obtained from this experiment are shown in FIG. 5.

After the respective elapses of 100 hr, 1400 hr and 1600 hr since the reaction starts, part of the catalyst slurry was drawn from the reactor to check the zinc sulfate concentration in the aqueous phase that is present in the reactor. The results are shown in Table 1.

TABLE 1

| Elapsed Time Since Reaction Starts | Concentration of Zinc Sulfate in Aqueous Phase (mol/liter) |
|---|---|
| 100 hr | 0.5 |
| 1400 hr (before further addition of zinc sulfate) | 0.5 |
| 1600 hr (after further addition of zinc sulfate) | 0.8 |

The continuous type experimental device employed in this example has a reactor with 3-liter capacity which inside surface is coated with Teflon, and is equipped with a separator incorporated into the inside of the reactor for separating the catalyst slurry and the formed oil containing unreacted benzene, which thus is designed to draw the formed oil containing unreacted benzene from the reactor. In order to prevent water and others in the catalyst slurry from decreasing by dissolving in the oil taken out of the system, the water and others in the oil were all recovered and appropiately returned to the reactor.

EXAMPLE 2

Figure 6:
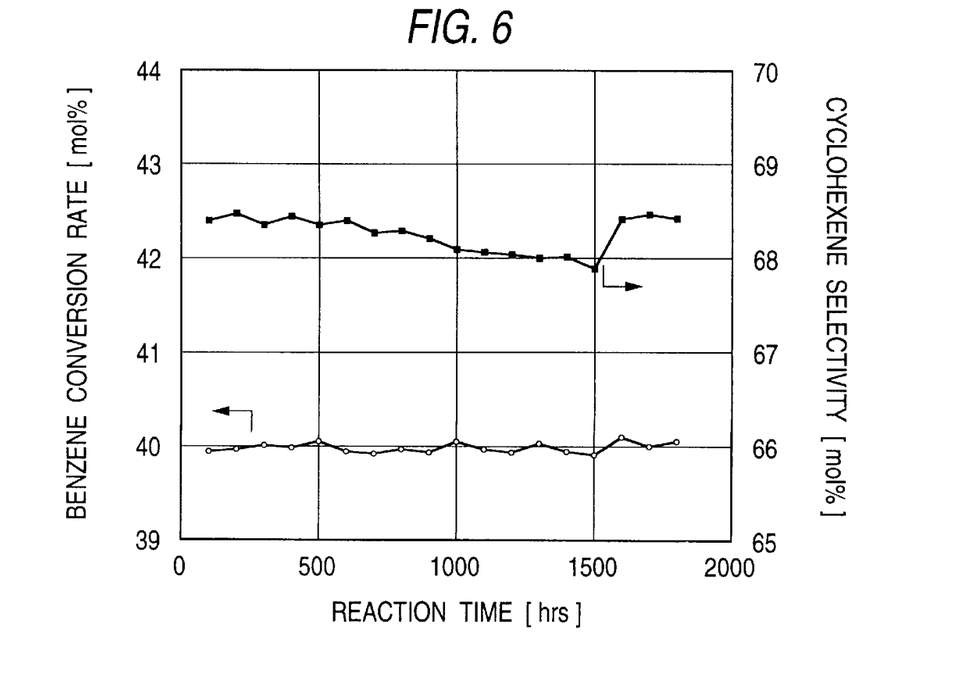
FIG. 6 is a graph showing the changes with time in the benzene conversion rate and in the cycloolefin selectivity which are calculated from the composition analyses of the oil drawn from the reactor in Example 2.

The reaction was carried out in the same manner as in Example 1, except that the ruthenium catalyst used in Example 1 was changed with that used in Reference Example 2. The results obtained are shown in FIG. 6 and Table 2.

TABLE 2

| Elapsed Time Since Reaction Starts | Concentration of Zinc Sulfate In Aqueous Phase (mol/liter) |
|---|---|
| 100 hr | 0.5 |
| 1400 hr (before further addition of zinc sulfate) | 0.5 |
| 1600 hr (after further addition of zinc sulfate) | 0.8 |

The results of Examples 1 and 2 show that the decrease in selectivity of cyclohexene with time can be inhibited by changing the concentration of zinc sulfate.

Thus, according to the present invention, a cycloolefin can be efficiently produced over a long period of time, while suppressing the decrease in the cycloolefin selectivity.

While the invention has been described in detail and with reference to specific examples thereof, it will be apparent to one skilled in the art that various changes and modifications can be made therein without departing from the spirit and scope thereof.

What is claimed is:

1. A process for producing a cycloolefin by partial hydrogenation of a monocyclic aromatic hydrocarbon with hydrogen in the presence of a ruthenium catalyst, water and a metal sulfate, in which:

said partial hydrogenation reaction has the maximum cycloolefin selectivity at an optimum concentration of the metal sulfate dissolved in an aqueous phase comprising the ruthenium catalyst used in said reaction, and said optimum metal sulfate concentration changes as the reaction proceeds, wherein said process comprises a step of adjusting the metal sulfate concentration in accordance with the change in the optimum metal sulfate concentration.

2. The process according to claim 1, wherein said adjustment is carried out by increasing the metal sulfate concentration after the reaction has proceeded for 100 hours.

3. The process according to claim 1, wherein said metal sulfate comprises at least zinc sulfate.

4. The process according to claim 1, wherein said metal sulfate concentration in the aqueous phase is changed within the range of from $1 \times 10^{-6}$ to 5.0 mol/liter.

5. The process according to claim 1, wherein said water is present in an amount of from 0.5 to 20 times by weight that of said monocyclic aromatic hydrocarbon.

6. The process according to claim 1, wherein said ruthenium catalyst comprises metallic ruthenium prepared by reducing a ruthenium compound beforehand.

7. The process according to claim 6, wherein said ruthenium catalyst is a non-supported catalyst and said metallic ruthenium has an average crystallite size of 200 Å or less.

8. The process according to claim 7, wherein said ruthenium compound comprises a zinc compound, and the content of zinc is from 0.1 to 50% by weight based on the weight of ruthenium.

9. A continuous process for producing a cycloolefin by partial hydrogenation of a monocyclic aromatic hydrocarbon with hydrogen in the presence of a ruthenium catalyst, water and a metal sulfate, in which:

said partial hydrogenation reaction shows the maximum cycloolefin selectivity at an optimum concentration of the metal sulfate dissolved in an aqueous phase comprising the ruthenium catalyst used in said reaction, and said optimum metal sulfate concentration changes over the course of the reaction, wherein said process comprises a step of adjusting the metal sulfate concentration in accordance with the change in the optimum metal sulfate concentration.

10. The process according to claim 4, wherein said partial hydrogenation reaction initially has a metal sulfate concentration in said aqueous phase of $1 \times 10^{-6}$M to 0.5M, and said metal sulfate concentration is increased to a concentration which is greater than 0.5M up to 5.0M after the reaction has been initiated.

11. The process according to claim 4, wherein said partial hydrogenation reaction initially has a metal sulfate concentration in said aqueous phase of $1 \times 10^{-6}$M to 0.5M, and said metal sulfate concentration is increased to a concentration which is greater than 0.8M up to 5.0M after the reaction has been initiated.

12. The process according to claim 4, wherein said partial hydrogenation reaction initially has a metal sulfate concentration in said aqueous phase of $1 \times 10^{-6}$M to 0.6M, and said metal sulfate concentration is increased to a concentration which is greater than 0.6M up to 5.0M after the reaction has been initiated.

* * * * *